United States Patent [19]

Marsh

[11] 4,327,036

[45] Apr. 27, 1982

[54] CHLORINATION PROCESS

[75] Inventor: Frank D. Marsh, Wilmington, Del.

[73] Assignee: E. I. Du Pont de Nemours and Company, Wilmington, Del.

[21] Appl. No.: 148,006

[22] Filed: May 8, 1980

[51] Int. Cl.$^3$ .................. C07C 121/50; C07B 9/00
[52] U.S. Cl. .................. 260/465 G; 260/466; 260/505 R; 260/961; 260/694; 546/98; 546/180; 560/18; 560/75; 560/83; 560/145; 562/602; 564/218; 564/442; 568/326; 568/335; 568/424; 568/656; 570/144; 570/207; 570/208; 570/209
[58] Field of Search .................. 260/694, 465 G; 570/208, 207, 209

[56] References Cited

U.S. PATENT DOCUMENTS

| | | | |
|---|---|---|---|
| 2,835,700 | 5/1958 | Boyle | 260/694 |
| 3,160,653 | 12/1964 | Benning et al. | 260/694 |
| 3,897,321 | 7/1975 | Blank et al. | 260/694 |
| 3,916,014 | 10/1975 | Nishihara et al. | 260/694 |
| 4,226,783 | 10/1980 | Marsh | 260/351 |

OTHER PUBLICATIONS

Renard et al., Chem. Reviews, 76,487–508 (1976).
Effenberger et al., Chem. Ber. 112, 1677–1688 (1979).
Chao et al., J. Org. Chem. 26, 1079–1081 (1961).
Scholl, Ber. 33, 723 (1900).
Goldschmidt et al., Ber. 58B, 566 (1925).
Chip et al., Canadian J. Chem. 50(8), 1233 (1972).

Primary Examiner—Ethel G. Love

[57] ABSTRACT

Process for nuclear chlorination of non-phenolic aromatic compounds, said process comprising contacting and reacting a non-phenolic aromatic compound having a net Hammett $\sigma$ value of about $-0.1$ to about 2.0 with chlorine monoxide in the presence of at least one-half an equivalent amount, based on the chlorine monoxide, of an acid having a $pK_a$ no greater than that of trichloroacetic acid, provided, however, when the net Hammett $\sigma$ value is about 0.7 to about 2.0, the acid has a $pK_a$ no greater than that of trifluoroacetic acid.

16 Claims, No Drawings

CHLORINATION PROCESS

DESCRIPTION

Technical Field

This invention relates to the chlorination of non-phenolic aromatic compounds with dichlorine monoxide, commonly referred to as chlorine monoxide, and, more particularly, to an improved process whereby nuclear substitution, that is, ring chlorination, is effected by means of dichlorine monoxide and an acid.

Background

Aromatic ring chlorination is an industrially important reaction but its scope is severely limited in that a large segment of aromatic compounds cannot be chlorinated readily. For example, chlorination of deactivated ring systems is a slow reaction normally requiring large amounts of catalyst and forcing conditions to achieve modest yields of mono- or dichlorinated derivatives.

Renard and Bolker, Chemical Reviews 76, 487–508 (1976), in summarizing the chemistry of chlorination by means of dichlorine monoxide, disclose the nuclear chlorination of phenols, cresols and anisole. They suggest that hypochlorous acid is formed during the chlorination, and that the use of 5% trichloroacetic acid increases the rate of chlorination of anisole.

Effenberger et al., Chem. Ber. 112, 1677–88 (1979), disclose the use of a mixture of dichlorine monoxide and trifluoromethanesulfonic acid anhydride in phosphorus oxychloride as a chlorinating agent at −18° to 40° C. for nitrobenzene, dinitrobenzene, chlorobenzene, toluene, o-xylene, trifluoromethylbenzene, benzonitrile and phthalonitrile.

Chao et al., J. Org. Chem. 26, 1079–1081 (1961), disclose the chlorination of N,N-dimethylaniline with dichlorine monoxide in carbon tetrachloride at 5°–15° C. for six hours to produce, in less than 25% yield, 2-, 4- and 2,4-chlorinated dimethylaniline.

Scholl, Ber. 33, 723 (1900) and Goldschmidt et al., Ber. 58B, 566 (1925), disclose the chlorination of benzene and indene by means of dichlorine monoxide.

Marsh, in, now U.S. Pat. No. 4,226,783, discloses a process for the chlorination of electronegatively substituted alkylaromatic compounds by means of dichlorine monoxide. The chlorination takes place at a saturated carbon atom attached to the aromatic nucleus and substituted with at least one hydrogen atom, to the substantial exclusion of aromatic ring chlorination.

DISCLOSURE OF INVENTION

For further comprehension of the invention and of the objects and advantages thereof, reference may be made to the following description and to the appended claims in which the various novel features of the invention are more particularly set forth.

The present invention resides in a process by which the aromatic nucleus of non-phenolic aromatic compounds can be controllably chlorinated in a relatively clean reaction providing high yields of the desired product without effecting to any substantial degree the chlorination of substituent groups having chlorine-replaceable hydrogen atoms. The process of this invention, therefore, may be seen to differ from the related process of the aforesaid copending application in that, even though dichlorine monoxide (hereinafter referred to as chlorine monoxide) provides the source of chlorine in both processes, aromatic ring chlorination is achieved in the instant process whereas side chain chlorination is effected in the related process. By non-phenolic aromatic compound is meant an aromatic compound which is devoid of an OH substituent attached to the aromatic nucleus. It is to be understood that the term does not preclude an acyloxy substituent attached to the aromatic nucleus. Consistent therewith, in the formula provided hereinafter, symbols A and B include

but not OH.

More specifically, the present invention resides in the discovery that chlorine monoxide in the presence of an acid, as hereinafter defined, is a powerful and selective chlorinating agent which can replace with chlorine one to all of the ring hydrogen atoms on substituted and unsubstituted non-phenolic aromatic compounds, as hereinafter defined, under relatively mild conditions, without effecting, to any substantial degree, the chlorination of any alkyl or substituted alkyl substituent on the ring. In carrying out the process of the invention using non-phenolic aromatic compounds having such alkyl substituents with one or more chlorine-replaceable hydrogen atoms, greater than 50%, very often 95–100%, on a molar basis, of the chlorination occurs on the aromatic ring. For example, when p-nitrotoluene is chlorinated by the process of the invention, one to four of the hydrogen atoms on the benzene ring can be controllably replaced with chlorine without substantially affecting the methyl substituent. The reaction proceeds cleanly, with water being the main by-product.

Non-phenolic aromatic systems which can be ring-chlorinated by the process of the invention include non-phenolic benzene, biphenyl, naphthalene, polynuclear aromatics and nitrogen-containing heteroaromatic systems. The aromatic ring can be substituted with electron-withdrawing (electronegative) groups, electron-donating (electropositive) groups, or both. The number of ring substituents which can be present depends on the nature of the substituents. In general, electron-donating substituents promote nuclear chlorination, electron-withdrawing substituents retard nuclear chlorination. Moreover, the extent of ring chlorination depends on the ring activity, that is, the electronic properties of the aromatic ring, and any combination of substituents per aromatic ring is operable provided the net effect of the summation of the Hammett $\sigma$ substituent values is within the range of about −0.1 to about 2.0.

The assessment of substituents by means of Hammett $\sigma$ values is well known to one skilled in the art. Publications in this field include "Physical Organic Chemistry," L. P. Hammett, 2nd ed, Chapter 11, McGraw-Hill, 1970; S. Ehrenson, R. T. C. Brownlee and R. W. Taft, Prog. Phys. Org. Chem., 10, 1 (1973); and M. Charton, ibid, 8, 235 (1971). Under this concept of considering the effect of a substituent, an electron-withdrawing substituent has a $\sigma$ value of greater than zero, an electron-donating substituent has a $\sigma$ value of less than zero.

The process of the invention requires the presence of an acid having a $pK_a$ no greater than that of trichloroacetic acid. A wide variety of acids are operable but, in general, stronger acids are required as the net effect of substituents on the aromatic nucleus goes from electron-donating to electron-withdrawing. In any event, the function of the acid is more than catalytic. It has been discovered that at least one half an equivalent of acid, based on the chlorine monoxide, must be used in the reaction. An excess over this amount commonly is used and is preferred. Usually, at least one equivalent of acid, based on the chlorine monoxide, is used in the reaction. To minimize side chain chlorination, a deficiency of acid and/or a gross excess of chlorine monoxide should be avoided. Operable protonic acids include sulfuric, trifluoromethanesulfonic (triflic), trifluoroacetic and perchloric acids. Lewis acids, such as boron trifluoride, antimony pentachloride and antimony trichloride, also are useful in the process of the invention. An acid which reacts detrimentally with the chlorine monoxide and/or the non-phenolic aromatic compound, thus competing with the desired chlorination reaction, is to be avoided.

It is to be understood that the $pK_a$ description provided herein is based on trichloroacetic acid and trifluoroacetic acid, rather than on specific $pK_a$ numerical values, since it is well known that the $pK_a$ value may vary with the solvent in which the $pK_a$ is determined.

The species formed by addition of chlorine monoxide to strong acid decomposes slowly at room temperature. Thus, a mixture of chlorine monoxide and trifluoromethanesulfonic acid in carbon tetrachloride, after being stirred five hours at 25° C., fails to chlorinate dimethyl terephthalate. The thermal stability of the reagent is a limiting factor for particularly unreactive aromatic compounds. If the aromatic compound being chlorinated is itself an acid, for example, an aromatic sulfonic acid, the process of the invention can be carried out without additional acid being present.

In addition to the acids noted above, other acids which are useful in the process of the invention include benzenesulfonic acid, p-toluenesulfonic acid, trichloroacetic acid, phosphoric acid, chlorosulfonic acid, chlorosulfonic acid/iodine, and nitric acid.

When the Hammett $\sigma$ value of the non-phenolic aromatic compound is within the range about 0.7 to about 2.0, the acid used should have a $pK_a$ no greater than that of trifluoroacetic acid. In general, and preferred, when the net effect of the substituents on the aromatic ring is electron-withdrawing, the acid should have a $pK_a$ no greater than that of trifluoroacetic acid. In preferred embodiments herein the $pK_a$ of the acid is no greater than that of trichloroacetic acid when the net Hammett $\sigma$ value is about −0.1 to about 2.0, no greater than that of trifluoroacetic acid when the net Hammett $\sigma$ value is about 0.7 to about 2.0, and the non-phenolic aromatic compound is of the formula selected from the group consisting of

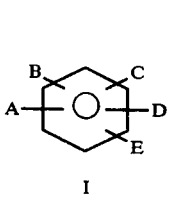
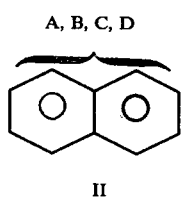

I        II

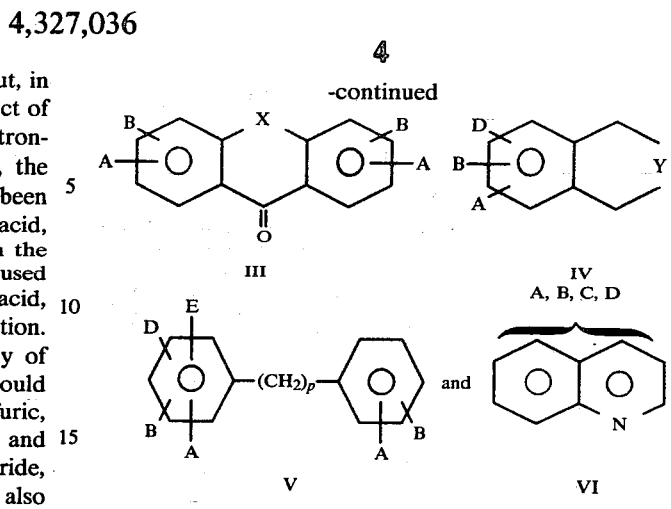

III     IV

V     VI wherein:
each of A and B is independently selected from H, OR, $OCF_3$, $NH_2$,

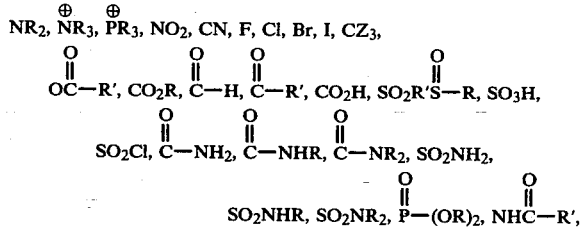

perfluoroalkyl of 1–8 carbon atoms, alkyl of 1–10 carbon atoms and alkyl of 1–10 carbon atoms substituted with any of the foregoing except H, perfluoroalkyl and alkyl;

C is H, OR, Cl, Br, F, $CZ_3$,

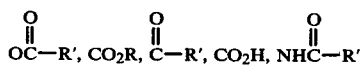

or alkyl of 1–10 carbon atoms;
D is H or Cl;
E is H or Cl;
R is alkyl of 1–10 carbon atoms or aryl;
R' is alkyl of 1–10 carbon atoms, aryl or $CZ_3$;
X is

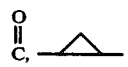

or $(CH_2)_n$;
Y is $(CH_2)_m$;
each Z is independently selected from Cl, Br, and F;
m is 3–6;
n is 0–3; and
p is 0–10,
provided, however, in III and V each of A and B is selected independently.

More preferred embodiments of the invention include the use of a non-phenolic aromatic compound of formula I as more specifically defined in the claims.

The process of the invention can be carried out in a variety of ways. Chlorine monoxide mixed with an inert carrier gas such as air or nitrogen can be passed into a solution of the aromatic compound in acid or a mixture of acid and an inert solvent such as carbon tetrachloride. For laboratory purposes, it is convenient to add solutions of chlorine monoxide in an inert solvent to the aromatic compound dissolved in an acid or a mixture of acid and an inert solvent. To achieve most efficient use of chlorine monoxide, it is advantageous to add this reagent slowly to the reaction mixture. Conversely, gaseous chlorine monoxide or a solution of chlorine monoxide in an inert solvent can be added to an acid, followed by addition of the aromatic compound. When this procedure is followed, the aromatic compound should be added soon after the reagents have been mixed.

Most of the chlorinations effected by the process of the invention, particularly of activated ring systems, are exothermic and can be carried out at $-40°$ to $100°$ C., but $0°$ to $50°$ C. is preferred. Perchlorination of strongly deactivated ring systems may require an excess of chlorine monoxide, a stong acid promoter, and temperatures up to $100°$ C. Superatmospheric pressure is not necessary, but it may be advantageous to carry out the process above atmospheric pressure at the high reaction temperatures to prevent loss of chlorine monoxide through vaporization from solution.

Chlorine orientation, on the aromatic nucleus, is governed by principles well known in the art. Electron-withdrawing substituents on the aromatic ring are meta-directing whereas elctron-donating substituents are ortho- and para-directing.

The following examples are intended to illustrate various embodiments of the invention. All temperatures reported are in degrees Centigrade.

EXAMPLE 1

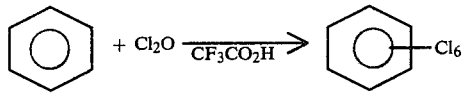

Chlorine monoxide (8.69 g, 0.1 mole) in carbon tetrachloride (112.3 ml) was added to trifluoroacetic acid (25 ml) while stirring and cooling at $-10°$. Benzene (1.95 g, 0.025 mole) was added slowly to the cold solution as the temperature rose to $12°$. After standing at room temperature for 3 days white needles separated. These were dissolved by adding additional carbon tetrachloride. The resulting solution was dried (MgSO$_4$) filtered and the volatiles removed from the filtrate on a rotary evaporator to give white crystalline hexachlorobenzene (7.28 g, yield 100%). The crude product was dissolved in methylene chloride and passed through a shallow bed of Florisil. The solvent was removed from the eluent on a rotary evaporator to give white needles (6.17 g) which were recrystallized from chloroform-petroleum ether to give pure hexachlorobenzene mp 234–235.8.

Anal. Calcd. for C$_6$Cl$_6$: C, 25.30; Cl, 74.70. Found: C, 25.79.

Mass spectrometric analysis of the product identified it as C$_6$Cl$_6$ (mol. wt. 284.8).

EXAMPLE 2

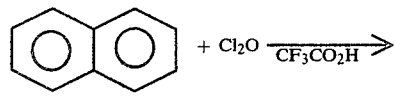

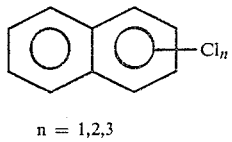

n = 1,2,3

To naphthalene (2.56 g, 0.02 mole) suspended in trifluoroacetic acid (20 ml) was slowly added chlorine monoxide (0.87 g, 0.01 mole) in carbon tetrachloride (13.5 ml) with stirring and cooling to maintain $22°$–$28°$. After stirring at room temperature overnight the reaction mixture was dried (MgSO$_4$), filtered and the solvent removed on a rotary evaporator to give a mixture of chloronaphthalenes (3.30 g). The mixture was separated by gas phase chromatography and the fractions identified by mass spectrometric analysis. The major products were mono- and dichloronaphthalene with small amounts of trichloronaphthalenes.

EXAMPLE 3

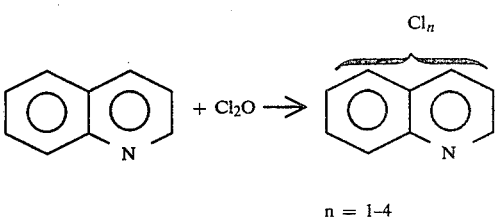

n = 1–4

To quinoline (1.29 g, 0.61 mole) in trifluoroacetic acid (12 ml) was added chlorine monoxide (3.48 g, 0.04 mole) in carbon tetrachloride (53 ml) at $10°$–$15°$ C. After stirring overnight at room temperature the mixture was diluted with methylene chloride and washed with sodium bicarbonate. The organic extract was dried and the solvent removed to give a tan powder (1.14 g). The product was separated by gas phase chromatography and the fractions shown by mass spectrometric analysis to contain unreacted quinoline (5%), monochloroquinoline (30%), dichloroquinoline (25%, 2 isomers), trichloroquinoline (14%, 2 isomers) and tetrachloroquinoline (24%).

EXAMPLE 4

The first part of this example illustrates the process of the invention whereas the second part of this example illustrates a process which is outside the invention because the strength of the acid and the amount of acid used (trichloroacetic acid) were insufficient.

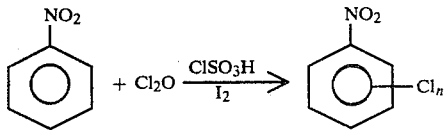

n = 3–5

To nitrobenzene (3.0 g, 0.024 mole) in chlorosulfonic acid (35 ml) and iodine (0.1 g) was slowly added chlorine monoxide (8.47 g, 0.098 mole) in carbon tetrachloride (93 ml) at $45°$–$50°$. The mixture was stirred and heated at $45°$–$50°$ for 1 hr after addition was complete. The product was poured into ice and extracted with methylene chloride. The extract was dried and the solvent removed on a rotary evaporator, to give a white solid (7.12 g). Analysis of the crude product by Hnmr and high pressure liquid chromatography (HPLC) showed it consisted largely of pentachloronitrobenzene (~60%), tetrachloronitrobenzene and a small amount of trichloronitrobenzene.

In a similar experiment nitrobenzene (2.0 g, 0.016 mole) in chlorosulfonic acid (25 ml) was reacted with chlorine monoxide (5.65 g, 0.065 mole) in carbon tetrachloride (90.7 ml) at 45° for 2 hrs. After stirring at room temperature overnight the product was isolated as described above to give light yellow oil 3.06 g. Analysis by Hnmr and HPLC showed a mixture of chloronitrobenzenes.

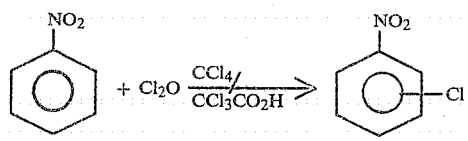

To nitrobenzene (1.23 g, 0.01 mole) in carbon tetrachloride (3 ml) was added chlorine monoxide (0.88 g, 0.01 mole) in carbon tetrachloride (10.4 ml). No exothermic reaction occurred. The mixture was stirred at room temperature for 3 days, dried and the solvents removed on a rotary evaporator to give a pale yellow oil (1.20 g). The Hnmr spectra of the recovered product was essentially identical with that of nitrobenzene. When this reaction was repeated using either a small amount of trichloroacetic acid (0.04 g, 5% based on $Cl_2O$) or two equivalents of the acid (3.27 g, 0.02 mole) nitrobenzene was recovered unchanged.

EXAMPLE 5

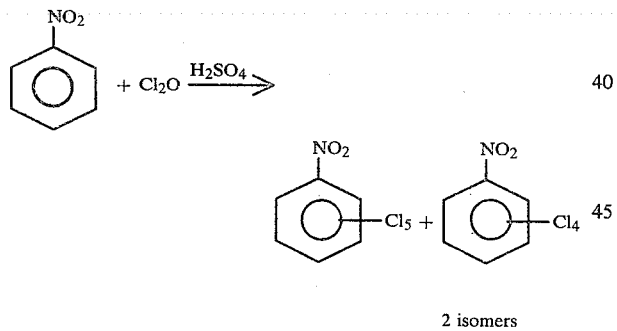

2 isomers

To nitrobenzene (3.0 g, 0.024 mole) in concentrated sulfuric acid (40 ml) was slowly added chlorine monoxide (8.47 g, 0.097 mole) in carbon tetrachloride (107 ml) at 35°–40°. Heating and stirring was continued for an additional 1.5 hrs. The mixture was poured into ice and extracted with methylene chloride. The extract was dried and the solvent removed on a rotary evaporator to give a white solid (6.50 g). The mixture was separated by gas phase chromatography and the fractions identified by mass spectrometric analysis as tetrachloronitrobenzene (2 isomers, 20.69% and 27.59%) and pentachloronitrobenzene (51.72%).

When a similar mixture of products was treated with excess chlorine monoxide at 45°–50° the crude product contained pentachloronitrobenzene (93.7% by HPLC analysis). One recrystallization from acetone-water gave pure pentachloronitrobenzene, mp 144–145.5. Purification by high pressure liquid chromatography (column 0.25 m, 6.2 mm id, packing, Zorbex ODS #149, carrier, 0.3% acetic acid, 50% acetonitrile, 50% water, flow 2.00 ml/min; 1300 psi) gave analytically pure product mp 145.4–146.4.

Anal. Calcd. for $C_6Cl_5NO_2$: C, 24.40; Cl, 60.02; N, 4.74; O, 10.83. Found: C, 24.59; Cl, 59.84; N, 4.49; 4.51.

Replacement of sulfuric acid by fuming sulfuric acid (20% $SO_3$) gave similar results.

EXAMPLE 6

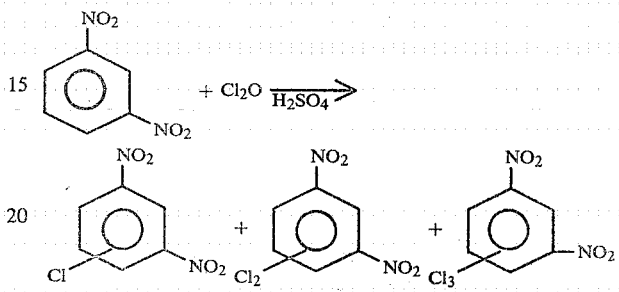

m-Dinitrobenzene (2.5 g moistened with water 20%, 0.019 mole) was dissolved in concentrated sulfuric acid (35 ml) and chlorine monoxide (4.14 g, 0.048 mole) in carbon tetrachloride was added slowly to maintain 25°–35°. The mixture was stirred at room temperature overnight and then poured onto ice. The mixture was extracted with methylene chloride, washed with aqueous sodium bicarbonate, dried and the solvent removed on a rotary evaporator to give a tan solid (3.04 g). The products were separated by gas-phase chromatography. Analysis of the fractions showed they consisted of chlorodinitrobenzene, dichlorodinitrobenzene, and small amounts of trichlorodinitrobenzene.

EXAMPLE 7

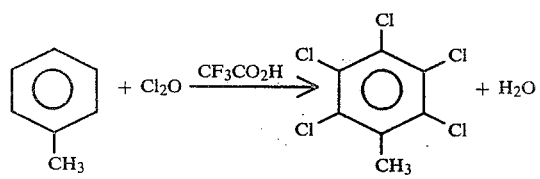

Chlorine monoxide (4.72 g, 0.054 mole) in carbon tetrachloride (50 ml) was added slowly to toluene (2.0 g, 0.022 mole) in trifluoroacetic acid (35 ml) with cooling to maintain 24°–25° C. When addition was complete the mixture was stirred to ambient temperature (20 min) and filtered to separate a white crystalline solid (2.92 g). The solvent was removed from the filtrate to give additional material (3.67 g). Recrystallization of the combined fractions from petroleum ether gave pure pentachlorotoluene mp 225–226.5.

$\delta^{CDCl_3/T}$ 2.65 singlet ($CH_3$)

| Measured m/e | Mass Spec Calcd. | Assignment |
|---|---|---|
| 261.4664 | 261.8677 | $C_7H_3Cl_5$ mol. ion. |

Under these conditions clean chlorination of the ring occurs to give the product in quantitative yield. However, if excess chlorine monoxide is used and the reaction is heated at 50° side chain chlorination also occurs.

EXAMPLE 8

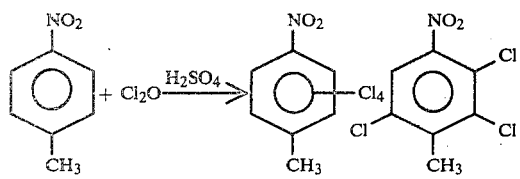

Chlorine monoxide (approximately 0.069 mole) diluted with two parts of air was passed directly into p-nitrotoluene (5.0 g, 0.037 mole) dissolved in concentrated sulfuric acid (25 ml) during 40 min. After standing overnight the mixture was poured onto ice and extracted with methylene chloride. The extract was washed with aqueous sodium bicarbonate, dried and the solvent removed on a rotary evaporator to give a crystalline solid (8.53 g). An aliquot (1.5 g) was purified by high pressure liquid chromatography (column −2X spheroids, 50 cm×2.5 cm ID; carrier 15% butyl chloride in cyclopentane; pressure 400 psi; flow 12 ml/min). Pure 2,3,5,6-tetrachloro-p-nitrotoluene (mp 152.9–154) was separated Anal. Calcd. for: C, 30.55; H, 1.10; N, 5.09; Cl, 51.59; O, 11.64. Found: C, 30.77; H, 1.24; N, 4.77 30.69; H, 1.22; N, 4.80.

$\delta^{CDCl_3}$/T 2.70 singlet—(CH$_3$)
$\gamma^{KBr}$

A second fraction (mp 55.6°–56.7° C.) was characterized as 2,3,5-trichloro-p-nitrotoluene by elemental analysis and spectral properties.

Anal. Calcd. for C$_7$HCl$_3$NO$_2$: C, 34.95; H, 1.68; N, 5.82; O, 13.31; Cl, 44.23. Found: C, 34.95; H, 1.73; N, 5.61;
Cl, 44.75
Cl, 44.75;
$\delta^{CDCl_3}$/Tmsi
2.68 H singlet (CH$_3$)
7.80 1H singlet (aromatic proton)
$\gamma^{KBr}$
3.25μ (=CH); 3.50 (sat CH); 6.54μ, 7.49μ (NO$_2$)

EXAMPLE 9

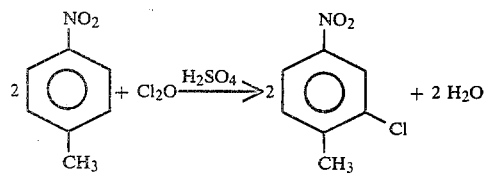

To p-nitrotoluene (8.3156 g, 0.0606 mole) in carbon tetrachloride (15 ml) and concentrated sulfuric acid (20 ml) was added chlorine monoxide (1.3175 g, 0.015 mol in 15 ml CCl$_4$) drop wise at a rate to maintain 25°–30° C. The mixture was stirred at room temperature overnight and then poured onto ice. The aqueous mixture was extracted with methylene chloride. The extract was dried and the solvent removed on a rotary evaporator to give a white solid which after evacuation at 0.1μ for several hours weighed 8.8787 g. Quantitative analysis of this product by HPLC using a calibrated column (i.e., using correction factors established from known mixtures of p-NT and 2-chloro-p-nitrotoluene) showed it contained p-nitrotoluene 32.8% and 2-chloro-p-nitrotoluene (58.8%). Since 2.007 moles of 2-chloro-4-nitrotoluene are formed for each mole of chlorine monoxide, it is apparent that both chlorines of chlorine monoxide are found in the product and water is assumed to be the by-product.

EXAMPLE 10

The first part of this example illustrates the process of the invention whereas the second part of this example illustrates a process which is outside the invention because the strength of the acid used (trichloroacetic acid) was insufficient.

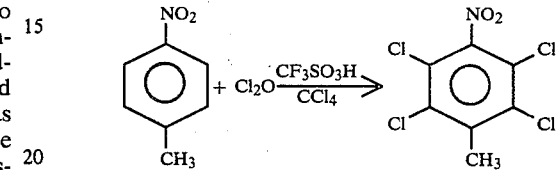

To a flask equipped with a magnetic stirrer, dropping funnel, thermometer condenser and nitrogen bubbler was added p-nitrotoluene (2.50 g, 0.0182 mol) carbon tetrachloride (10 ml) and trifluoromethane sulfonic acid (10.91 g, 0.072 mole). The mixture was stirred and cooled to maintain 35°–45° C. as chlorine monoxide (6.32 g, 0.0727 mole) in carbon tetrachloride (67.5 ml) was added during 35 min. Stirring was continued for 3 hrs and the mixture was poured onto ice. The resulting mixture was extracted with methylene chloride. The extract was washed with aqueous sodium bicarbonate, dried and the solvent removed on a rotary evaporator to give a white solid (6.53 g). Recrystallization from acetone-water gave pure tetrachloro-p-nitrotoluene mp 150.6–151.6.

Anal. Calcd. for C$_7$H$_3$NO$_2$Cl$_4$: C, 30.58; H, 1.10; N, 5.09; O, 11.64; Cl, 51.59. Found: C, 30.92; H, 1.29; N, 4.99 C, 30.83; H, 1.27; N, 4.83.

$\delta^{CDCl_3}$/T 2.66 singlet
$\gamma^{KBr}$ weak 3.45μ (CH$_3$); 6.44μ, 7.40μ (NO$_2$).

This reaction was carried out on larger scale using p-nitrotoluene (28.64 g, 0.208 mole) Cl$_2$O (63.53 g, 0.73 mole), carbon tetrachloride 845 ml and concentrated sulfuric acid (125 ml) to give the crude product (55.8 g) in 97.3% yield.

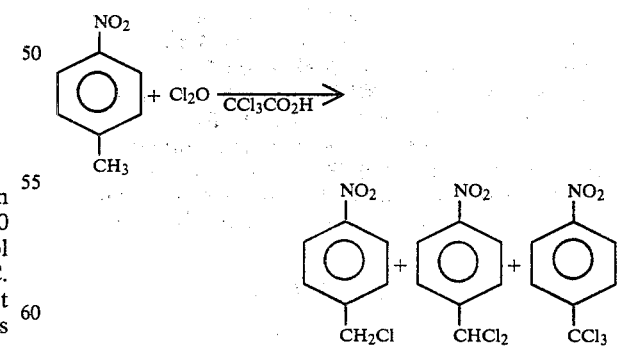

To p-nitrotoluene (1.37 g, 0.01 mole) in carbon tetrachloride (3 ml) and trichloroacetic acid (0.09 g, 5% based on Cl$_2$O) was added chlorine monoxide (1.83 g, 0.021 mole) in carbon tetrachloride (22 ml). After stirring three days at ambient temperature the reaction mixture was washed with aqueous sodium bicarbonate until the wash remained basic. The organic layer was dried and the solvent removed on a rotary evaporator to give clear mobile oil (1.95 g). Hnmr analysis of the product showed it contained p-nitrotoluene (25%), p-nitrobenzylchloride (3.8%), p-nitrobenzal chloride (12.6%), and p-nitrobenzotrichloride (81.2%).

When this experiment was repeated using two equivalents of trichloroacetic acid (6.86 g, 0.042 mole) similar side chain chlorination products were formed and identified by Hnmr analysis of the mixture.

EXAMPLE 11

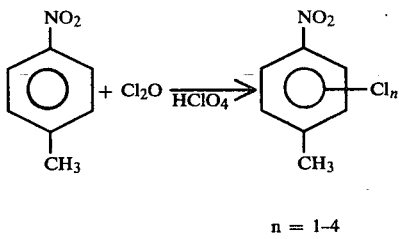

n = 1–4

To p-nitrotoluene (2.74 g, 0.02 mole) suspended in perchloric acid (70%, 20 ml) was slowly added chlorine monoxide (0.87 g, 0.01 mole) in carbon tetrachloride (12.5 ml) with stirring and cooling to maintain 25°–30°. The reaction mixture was extracted with methylene chloride. The extract was dried and the solvent removed on a rotary evaporator to give a white crystalline solid (4.37 g). The product was separated by gas phase chromatography. The main fractions, identified by mass spectrometric analysis, and Hnmr were monochloro-p-nitrotoluene (87%), unreacted p-nitrotoluene (8.5%) and small amounts of di, tri, and tetrachloro-p-nitrotoluenes.

EXAMPLE 12

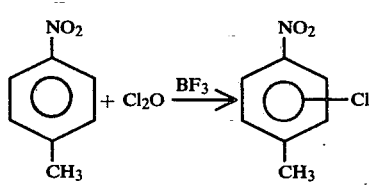

p-Nitrotoluene (2.10 g, 0.015 mole) in carbon tetrachloride (25 ml) was saturated with borontrifluoride and a slow flow of this gas was maintained while slowly adding chlorine monoxide (0.64 g, 0.007 mole) in carbon tetrachloride (8 ml). When addition was complete the borontrifluoride flow was stopped. The mixture was stirred at room temperature overnight, poured onto ice and extracted with methylene chloride. The extract was dried and the solvent removed to give a white solid (2.44 g). Analysis by Hnmr showed the presence of chloronitrotoluene.

EXAMPLE 13

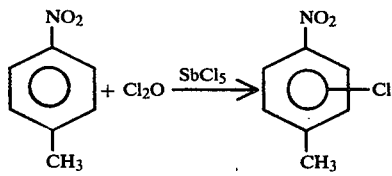

To p-nitrotoluene (2.0 g, 0.015 mole) in carbon tetrachloride (20 ml) was added antimony pentachloride (6.0 ml, 0.06 mole). A yellow slurry was formed in an exothermic reaction. The mixture was stirred at 25°–26° while adding chlorine monoxide (5.07 g, 0.06 mole) in carbon tetrachloride (60 ml). The mixture was stirred at room temperature for 2 hrs poured onto ice, and extracted with methylene chloride. The extract was dried and the solvent removed to give a light yellow solid (2.55 g). The Hnmr spectra was essentially identical with that of an authentic sample of 2-chloronitrotoluene.

EXAMPLE 14

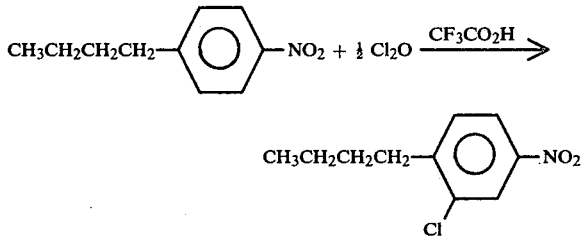

Trifluoroacetic acid (10 ml) was cooled to 0° and treated with a solution of $Cl_2O$ in $CCl_4$ (5 ml, 5.0 mmol). The resulting solution was treated dropwise with a solution of 4-n-butylnitrobenzene (1.61 g, 9.0 mmol) in $CCl_4$ (3 ml), stirred for 0.5 hr at 5° and then at 25° for 1.5 hr. The mixture was added to water and extracted with $CCl_4$. The organic layer was washed with sodium bicarbonate, saturated sodium chloride, dried ($MgSO_4$), and evaporated to give 2.03 g of residue. Kugelrohr distillation gave 1.85 g of light yellow oil, bp 90° (0.2 mm). $^1H$ nmr: $\delta^{TMS}_{CDCl_3}$ 8.07 (d, J=2.1 Hz), 7.92 (dd,J=2.1 Hz, 8.4 Hz), 7.28 (d,J=8.4 Hz), 2.78 (t,J=6.6 Hz), 1.80–1.20 (m) and 1.10–0.85 (m), consistent with 4-n-butyl-3-chloronitrobenzene.

EXAMPLE 15

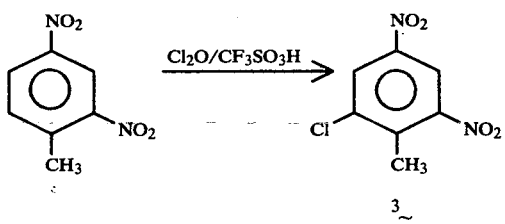

A mixture of 2,4-dinitrotoluene (5.93 g, 32.6 mmol), trifluoromethanesulfonic acid (2.86 ml) and $CCl_4$ (16 ml) was treated with a solution of $Cl_2O$ in $CCl_4$ between 20° and 30°. After 2.0 hr, the mixture was purged with a stream of nitrogen, added to water and extracted with $CH_2Cl_2$. The organic layer was washed with bicarbonate solution, brine, and dried. Evaporation provided 6.9 g of crude product which was recrystallized from pet. ether/ether to give 4.5 g, mp 46°–48°. $^1H$ nmr: 8.60–8.45 (m), 2.63 (s). Calcd. for $C_7H_5ClN_2O_4$: 215.9937; found 215.9931.

Anal. Calcd.: C, 38.82; H, 2.33; N, 12.93; Cl, 16.37. Found: C, 38.65; H, 2.36; N, 12.75; Cl, 16.41.

EXAMPLE 16

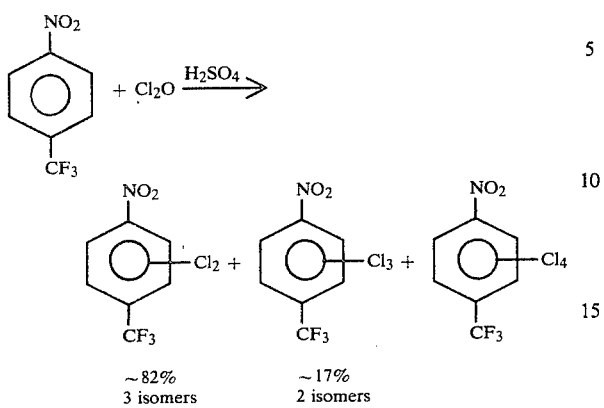

~82%
3 isomers

~17%
2 isomers

Chlorine monoxide (7.25 g, 0.08 mole) in carbon tetrachloride (77 ml) was added slowly to p-nitrobenzotrifluoride (4.0 g, 0.02 mole) in concentrated sulfuric acid (35 ml) at 45°–50°. The mixture was stirred at 45° for an additional 0.5 hr. The layers were separated and the organic layer was washed with aqueous sodium bicarbonate, dried and the solvent removed to give a mobile oil (5.33 g).

The product was separated by gas-phase chromatography and the fractions when characterized by mass spectrometric analysis, consisted largely of dichloro-p-nitrobenzotrifluoride (73%, 3 isomers) trichloro-p-nitrobenzotrifluoride (~25%, two isomers) and a small amount of tetrachloro-p-nitrobenzotrifluoride. Further reaction with chlorine monoxide under similar conditions increased the yield of the tetrachloro-p-nitrobenzotrifluoride.

EXAMPLE 17

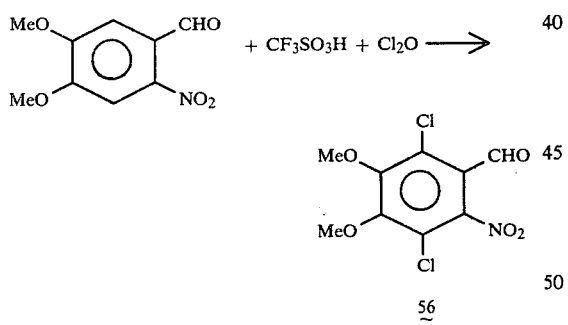

56

A slurry of 6-nitroveratraldehyde (4.89 g, 30 mmol) in $CCl_4$ (60 ml) at ca. 5° was treated with trifluoromethanesulfonic acid (2.84 ml, 31.5 mmol). The resulting mixture was treated dropwise with a solution of dichlorine monoxide in $CCl_4$ (35 ml, 31.5 mmol). When addition was complete, the mixture was allowed to warm slowly to 35°. The mixture was stirred at ambient temperature for 3.0 hr, added to water (250 ml) and extracted with $CH_2Cl_2$. The organic layer was washed with water, saturated sodium chloride solution, dried ($MgSO_4$), and evaporated to give 6.4 g of red solid. The sample was recrystallized twice from ether to provide 2.19 g of yellow solid, mp 119°–122°. Mother liquors were processed to give an additional 0.94 g of product. $^1H$ nmr: 10.28 (s, C$\underline{H}$O), 4.09 (s, OC$\underline{H}_3$), 4.00 (s, OC$\underline{H}_3$). UV $\lambda_{max}$ 320 nm (sh, $\epsilon$=845), 270 nm (sh, $\epsilon$=3090), 210 nm ($\epsilon$=36,200). Mass spec calcd for $C_9H_7Cl_2NO_5$, 278.97–0. Measured, 278.9728.

Anal. Calcd: C, 38.60, H, 2.52; N, 5.00; Cl, 25.32. Found: C, 38.82; H, 2.66; N, 4.81; Cl, 25.24. C, 38.79 H, 2.69 N, 4.85 Cl, 25.34.

EXAMPLE 18

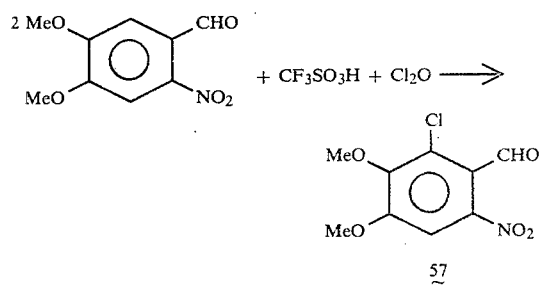

57

A solution of 6-niroveratraldehyde (2.52 g, 15.5 mmol) in $CH_2Cl_2$ (30 ml) at 0° was treated with trifluoromethanesulfonic acid (0.74 ml, 8 mmol) and then with a solution of dichlorine monoxide in $CCl_4$ (8.1 mmol) during which the temperature reached 10°. The mixture was stirred for 2.0 hr at ambient temperature, added to water and extracted with $CH_2Cl_2$. The organic phase was washed with water, saturated sodium chloride, and dried to give a yellow solid whose nmr spectrum showed a mixture of starting aldehyde and one monochloroaldehyde. Recrystallization from ethanol provided 1.32 g of yellow solid, mp 125°–126°. $^1H$ nmr: 10.25 (s, C$\underline{H}$O), 7.47 (s, aryl C$\underline{H}$), 4.02 and 3.98 (s, OC$\underline{H}_3$). UV $\lambda_{max}$ 288 nm ($\epsilon$=5050), 239 nm ($\epsilon$=12,300). The mother liquors consisted of a mixture of aldehydes (minor) and the corresponding diethyl acetals.

EXAMPLE 19

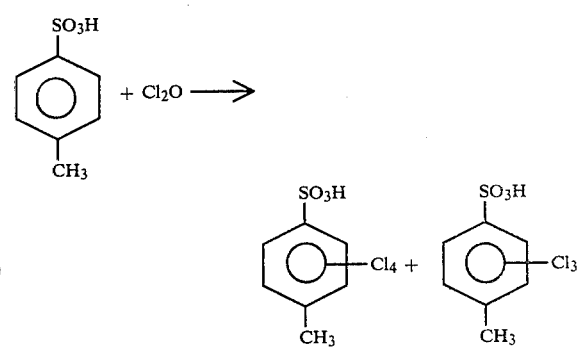

To p-toluene sulfonic acid monohydrate (3.10 g, 0.016 mole) in a Carrius tube was added chlorine monoxide (4.25 g, 0.049 mole) in carbon tetrachloride (60 ml). The tube was immediately cooled in liquid nitrogen, evacuated, sealed and then heated at 75° for 19.5 hrs. After cooling to room temperature the tube was opened and the contents filtered to separate a white solid which after drying under vacuum over $P_2O_5$ weighed 4.50 g. Evaporation of the filtrate to dryness gave additional product (0.89 g). The Hnmr spectron in deutero acetone showed two singlets (3H, $\delta$ 2.5, 2.6; $CH_3$) of approximately equal weight; a singlet at $\delta$ 8.1 (1H, aromatic proton) and an exchangeable singlet (1H, $\delta$ 9.67; $SO_3H$). The product was judged to be an approximately equal mixture of tetrachloro- and trichloro-p-toluenesulfonic acid. Mass spectrometric analysis of the product obtained from a similar run showed the presence of two products, C₇H₅SO₃Cl₃ (m/e 274) and C₇H₄SO₃Cl₄ (m/e 308).

EXAMPLE 20

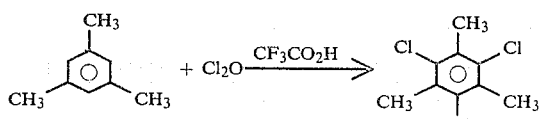

Chlorine monoxide (3.26 g, 0.038 mole) in carbon tetrachloride (38.7 ml) was added dropwise to mesitylene (3.0 g, 0.025 mole) in trifluoroacetic acid (35 ml) during 20 minutes with stirring and cooling to maintain 25°–30°.

After standing at room temperature for several days white crystalline 2,4,6-trichloromesitylene (3.89 g) was separated by filtration. The filtrate was dried (MgSO₄), filtered and the solvent removed to separate additional product (1.53 g, yield 97.3%).

$\delta^{CDCl_3}$/Tmsi 2.42 singlet

One recrystallization from 1-chlorobutane gave analytically pure product mp 214–216.3.

Anal. Calcd. for C₉H₉Cl₃: C, 48.36; H, 4.06; Cl, 47.58. Found: C, 48.51; H, 4.34; Cl, 47.54.

$\gamma^{KBr}$ 2920, 2860 cm⁻¹ (sat CH)

1550 cm⁻¹ (aromatic C=C)

Analysis by gas phase chromatography and mass spectrometry showed the product to be pure trichloromesitylene m wt. 223.5.

EXAMPLE 21

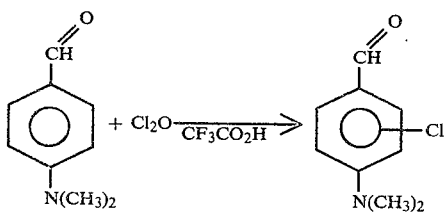

To p-aminobenzaldehyde (2.98 g, 0.02 mole) in trifluoroacetic acid (15 ml) was slowly added chlorine monoxide (0.96 g, 0.011 mole) in carbon tetrachloride (12 ml) with stirring and cooling to maintain 25°–35° C. When addition was complete the mixture was heated at 45° for 1 hr. After standing at room temperature overnight the mixture was diluted with methylene chloride and washed with aqueous sodium bicarbonate and then with water. The solution was dried and the volatiles removed on a rotary evaporator to give an oil (1.07 g). Analysis by H nmr showed a mixture of ring chlorinated products was obtained.

EXAMPLE 22

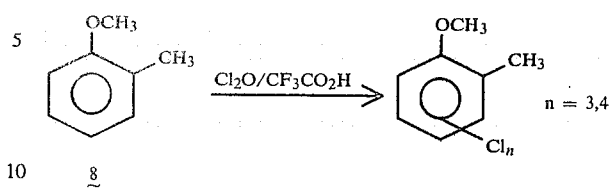

(A) A solution of 2L-methylanisole (2.44 g, 20 mmol), in CCl₄ (15 ml) was cooled to 10° and treated with trifluoroacetic acid (3.1 ml, 40 mmol). A solution of Cl₂O in CCl₄ (36 ml, 40 mmol) was added dropwise below 10° and the mixture was stirred for an additional 0.5 hr. The mixture was washed twice with water (50 ml), brine, dried (MgSO₄), and evaporated to give 4.28 g of yellow oil. ¹H nmr 7.35 (s), 7.20 (s), 3.82 (s), 2.40 (s), 2.30 (s), 2.15-1.8 (m). GC-mass spec showed that the product consisted mainly (~90%) of a mixture of two trichloro-compounds.

(B) The reaction was repeated as in (A) above, except that 50 mmol quantities of trifluoroacetic acid and Cl₂O were employed. The mixture was stirred for 2.5 hr before work-up. Glpc analysis (3% SE-30, 6'×¼") showed two majore components in a ca. 60/40 ratio. Several minor components were also present. Recrystallization from pet. ether gave 1.0 g (mp 75–85%). ¹H nmr: 7.35 (s), 3.82 (s), 2.38 (s), consistent with a 70/30 mixture of tetrachloro/trichloro derivatives. GC-mass spectral analysis showed one trichloro derivative and the tetrachloro compound.

EXAMPLE 23

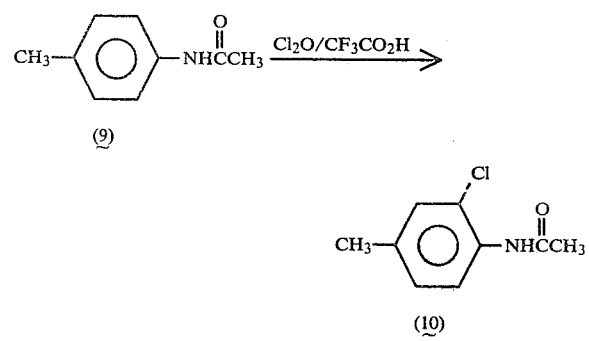

Trifluoroacetic acid (2.34 ml, 30 mmol) was added to a solution of 4-methylacetanilide (2.24 g, 15 mmol) in CH₂Cl₂ (15 ml). A solution of Cl₂O in CCl₄ (14 ml, 15 mmol) was added dropwise and the mixture was stirred for 3 hr. The mixture was added to water and neutralized by addition of bicarbonate. The organic layer was washed well with bisulfite solution, brine, and dried. Evaporation gave 2.59 g of tan solid. Recrystallization (twice) from ether gave 1.14 g of solid, mp 101°–103°. ¹H nmr: 8.10 (d,J=8.5 Hz), 7.83–7.33 (broad s), 7.25–6.92 (m), 2.28 and 2.18 (singlets), consistent with the assigned structure 10.

EXAMPLE 24

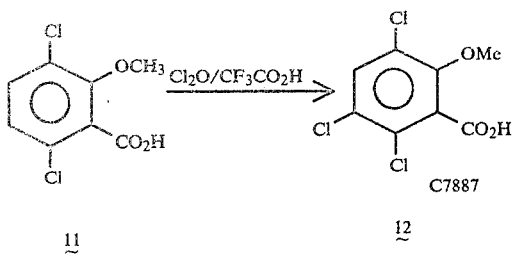

A solution of 3,6-dichloro-2-methoxybenzoic acid (3.32 q, 15 mmol) in CH$_2$Cl$_2$ (15 ml) was treated with trifluoroacetic acid (2.34 ml, 30 mmol) and the resulting solution was treated with a solution of Cl$_2$O in CCl$_4$ (30 mmol) while the temperature was maintained at ca. 30°. The mixture was stirred for 3 hr, added to water and extracted with CH$_2$cl$_2$. Combined extracts were washed with water, brine, dried and evaporated to give 3.83 g of solid. Recrystallization from toluene/hexane gave 1.77 g of cream-colored solid, mp 127°–134°. $^1$H nmr 10.87 (s, O$\underline{H}$, 7.58 (s, C$\underline{H}$), 3.97 (s, OC$\underline{H}_3$). Product was taken up in 1.0 N NaOH and re-precipitated by addition of dilute acid to give a sample with mp 133°–135°.

Anal. Calcd. for C$_8$H$_5$Cl$_3$O$_3$: C, 37.61; H, 1.97; Cl, 41.63. Found: C, 37.78; H, 1.92; Cl, 41.29 C, 37.71 H, 2.13 Cl, 41.26

EXAMPLE 25

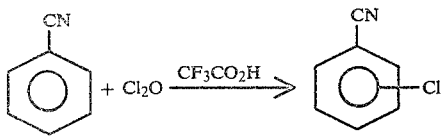

Chlorine monoxide (1.26 g, 0.015 mole) in carbon tetrachloride (13 ml) was added dropwise to benzonitrile (3.0 g, 0.029 mole) in trifluoroacetic acid (25 ml) at 20°–25° C. The mixture was stirred at room temperature for 1 hr after addition was complete. The majority of the solvent was removed on a rotary evaporator. The residue was dissolved in methylene chloride, washed with aqueous sodium bicarbonate, dried and the solvent removed to give a light brown oil (1.27 g).

The mixture was separated by gas phase chromatography and the fractions identified by mass spectrometric analysis. The major products were mono- and di-chlorobenzonitriles and chlorobenzamides.

EXAMPLE 26

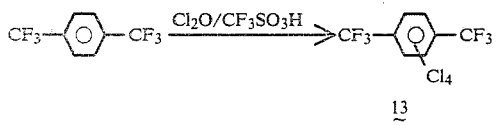

A mixture of 1,4-bis(trifluoromethyl)benzene (6.42 g, 30 mmol), trifluoromethane sulfonic acid (7.9 ml, 90 mmol), and CCl$_4$ (10 ml) was treated dropwise with a solution of Cl$_2$O in CCl$_4$ (100 ml, 100 mmol). The temperature was kept at ca. 30° during the first half of the Cl$_2$O addition. The mixture was stirred at room temperature for 2.5 hr, then purged with a stream of nitrogen, added to 300 ml water and extracted with CH$_2$Cl$_2$. The organic layer was washed several times with sodium bicarbonate, brine, dried (MgSo$_4$), and evaporated to provide 10.5 g of yellow oil. The product was distilled to remove mono-, di-, and trichloro derivatives (25°–50° at 0.2 mm) and the pot residue was Kugelrohr distilled to give 2.95 g of white solid. Recrystallization (MeOH) gave 1.95 g of white solid, mp 46°–48°.

Anal. Calcd.: C, 27.31; Cl, 40.30. Found: C, 27.37; Cl, 40.24 Cl, 40.23.

EXAMPLE 27

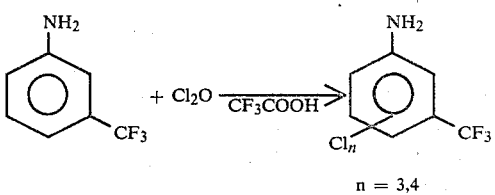

n = 3,4

Chlorine monoxide (1.74 g, 0.01 mole) in carbon tetrachloride (22.5 ml) was added dropwise to α,α,α-trifluoromethyl-m-toluidine dissolved in trifluoroacetic acid (20 ml) with stirring and cooling to maintain 25°–32°. The reaction mixture was dried (MgSO$_4$) filtered and the volatiles removed on a rotary evaporator to give a brown solid (6.27 g). This solid was dissolved in methylene chloride and washed with aqueous sodium bicarbonate until the solution remained basic. The organic layer was dried and the solvent removed on a rotary evaporator to give a brown oil (2.59 g).

The main products were separated by gas phase chromatography and identified by mass spectrometric analysis as trichloro-α,α,α-trifluoro-m-toluidine (34%), tetrachloro-α,α,α-trifluoro-m-toluidine (37%).

EXAMPLE 28

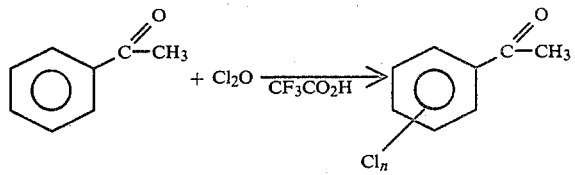

To acetophenone (3.0 g, 0.025 mole) in trifluoroacetic acid (35 ml) was slowly added chlorine monoxide (1.09 g, 0.013 mole) in carbon tetrachloride (13 ml) at 45°–50° C. Reaction was rapid as judged by disappearance of characteristic brown chlorine monoxide color. The mixture was diluted with methylene chloride, and washed with aqueous sodium bicarbonate. The organic layer was dried and the solvent removed to give a light yellow oil (3.22 g). Hnmr analysis suggested ring chlorination and some reaction at the methyl carbon.

EXAMPLE 29

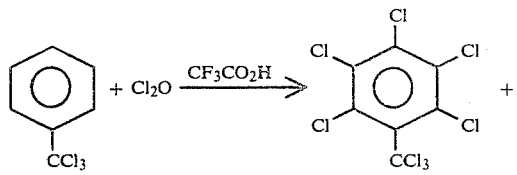

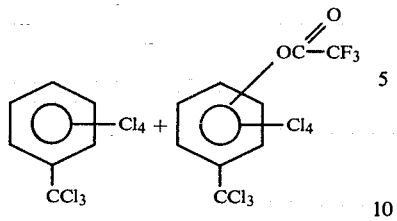

Four equivalents of chlorine monoxide (7.11 g, 0.081 mole) in carbon tetrachloride (75 ml) were added slowly to ααα-trichlorotoluene (4.0 g, 0.0205 mole) in trifluoroacetic acid (35 ml) at ~10° C. When addition was complete the solution was warmed to 50° and the solvent was then removed on a rotary evaporator to give a light yellow solid (6.19 g). The products were separated by gas phase chromatography. Mass spectrometric analysis of the fractions showed they consisted of isomeric heptachlorotoluenes, octachlorotoluene and a small amount of a heptachlorotoluene containing a trifluoromethylacetyl substituent. Further treatment of the product with excess monoxide at 50° C. gave an oil believed to be largely octachlorotroluene.

EXAMPLE 30

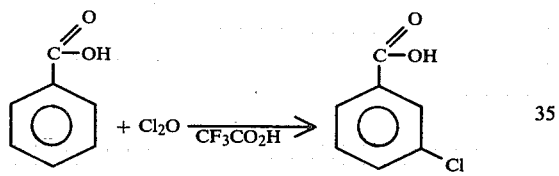

Chlorine monoxide (1.09 g, 0.0125 mole) in carbon tetrachloride (12.9 ml) was added during 11 minutes to benzoic acid (3.05 g, 0.025 mole) in trifluoroacetic acid (35 ml) with stirring and cooling to maintain 25°–31° C. After standing at room temperature for several days the mixture was filtered to separate white crystalline chlorobenzoic acid (0.34 g). The filtrate was dried (MgSO₄) filtered and the volatiles removed on a rotary evaporator to give additional product (3.38 g). Gas phase chromatography followed by mass spectrometric analysis of the fractions showed the product consisted of chlorobenzoic acid (90%) and unreacted benzoic acid (10%).

δCDCl₃/Tmsi 7.2–8.15 (aromatic protons)

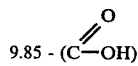

EXAMPLE 31

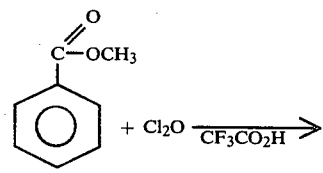

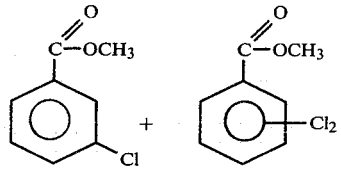

Chlorine monoxide (1.09 g, 0.0125 mole) in carbon tetrachloride (12.9 ml) was added during 12 minutes to methylbenzoate (3.40 g, 0.025 mole) in trifluoroacetic acid (25 ml) with stirring and cooling to maintain 25°–30°. After standing several days at room temperature the mixture was dried (MgSO₄) filtered and volatiles removed on a rotary evaporator to give a mobile oil (4.5 g).

δCDCl₃/Tmsi 3.85, singlet (OCH₃)
7.10–8.0 Complex group (aromatic protons)

Gas phase chromatography followed by mass spectrometric analysis of the fractions showed recovered methylbenzoate (22.08%), chloromethylbenzoate (54.13%), and two isomeric dichloromethylbenzoates (7.92%) and small amounts of later eluting products which were not identified.

This reaction was repeated using chlorine monoxide (4.35 g, 0.05 mole) in carbon tetrachloride (51.9 ml), methylbenzoate (1.70 g, 0.0125 mole) and trifluoroacetic acid (50 ml). The product when analyzed as described above consisted of pentachloromethylbenzoate (69%) and hexachlorobenzene (33%).

EXAMPLE 32

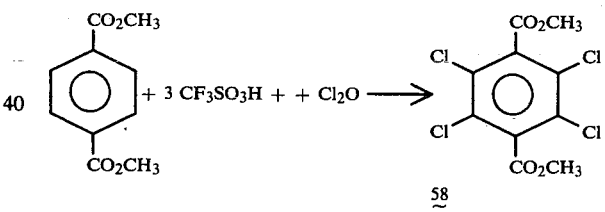

A mixture of dimethylterephthalate (3.88 g, 20 mmol) in CH₂Cl₂ (60 ml) at 0°–5° was treated with trifluoromethanesulfonic acid (5.25 ml, 60 mmol) and then dropwise with a solution of Cl₂O in CCl₄ (66 ml, 60 mmol) over a 15 min interval. When addition was complete, the ice bath was removed and the mixture stirred at ambient temperature for 4.5 hr. The mixture was purged with a stream of N₂ for 0.5 hr, added to water (150 ml) and extracted twice with CH₂Cl₂. Combined extracts were washed with bicarbonate solution and NaCl solution, dried (MgSO₄), and evaporated to give ca. 6.9 g of white solid. Glpc analysis (6'×¼" 3% SE-30 at 150°–240°) showed 95% tetra chloro ester 58. Recrystallization (MeOH) gave 5.75 g of crystals, mp 157°–158°. ¹H nmr: 4.03 (s, OC$\underline{H}$₃).

EXAMPLE 33

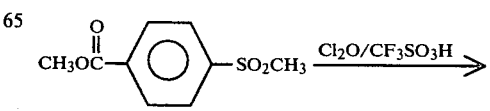

-continued

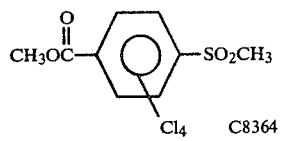

14

A solution of methyl 4-(methylsulfonyl)benzoate (1.88 g, 8.8 mmol) in CH$_2$Cl$_2$ (20 ml) was cooled and treated with trifluoromethanesulfonic acid (2.63 ml, 30 mmol). The resulting mixture was treated dropwise with a solution of Cl$_2$O in CCl$_4$ (66 ml, 60 mmol) while the temperature was allowed to increase to 35°. The mixture was stirred for 3.0 hr, purged with a stream of nitrogen, added to 150 ml water, and extracted twice with CH$_2$Cl$_2$. Combined extracts were washed with bicarbonate solution, brine, and dired. Evaporation gave 2.9 g of white solid. $^1$H nmr: 4.05 (s), 3.42 (s). Recrystallization gave 1.8 g, mp 193°–194°.

Anal. Calcd for C$_9$H$_6$Cl$_4$O$_4$S: C, 30.71; H, 1.72. Found: C, 30.81; H, 1.94. C, 30.66 H, 1.79.

EXAMPLE 34

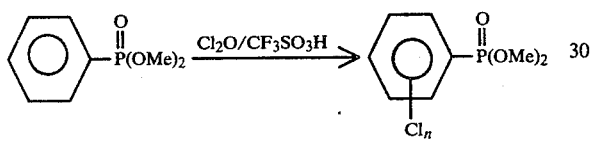

A solution of dimethyl phenylphosphonate (1.58 g, 8.5 mmol) in CCl$_4$ (10 ml) at 5° was treated with trifluoromethanesulfonic acid (2.25 ml, 26 mmol). A solution of Cl$_2$O in CCl$_4$ (26 mmol) was added dropwise while the temperature was maintained at 25;20 -30°. After 1.0 hr at 25°, the mixture was added to water and extracted with CH$_2$Cl$_2$. The extract was washed with bicarbonate solution, brine, and dried. Evaporation gave 2.42 g of solid. Recrystallization (hexane/CH$_2$Cl$_2$) gave a white solid, mp 104°–109°. $^1$H nmr δTMS/CDCl$_3$ 7.77 (s) and 3.88 (d, J=11.5 Hz) consistent with dimethyl 2,3,5,6-tetrachlorophenylphosphonate. Mass spectrum: measured 321.8864, calcd for C$_8$H$_7$Cl$_4$O$_3$P 321.8888. Also produced were small amounts of the 2,3,4,5-tetrachlorophenyl- and pentachlorophenylphosphonates.

EXAMPLE 35

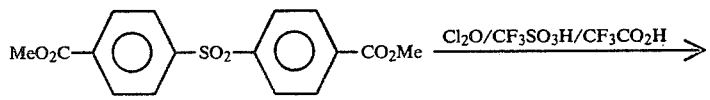

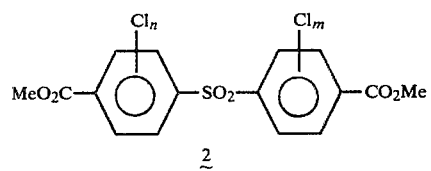

A solution of the diester 1 (3.34 g, 10 mmol) in trifluoroacetic acid (25 ml) was treated with trifluoromethanesulfonic acid (~1.0 ml) and then dropwise with a solution of Cl$_2$O in CCl$_4$ (62 ml, 50 mmol). After ca. 2.0 hr, the mixture was added to water (200 ml) and extracted twice with CH$_2$Cl$_2$. Combined extracts were washed several times with bicarbonate solution, brine, and dried. Evaporation gave 5.05 g of white solid. $^1$H nmr analysis showed that the average number of chlorine atoms per molecule was three. The crude product was recrystallized twice from methanol and once from ethanol to give 1.10 g, mp 172°–174° which was a mixture of tri- and tetrachloro derivatives.

Mass spectrum: Calcd. for C$_{16}$H$_{10}$Cl$_4$O$_6$S: 469.8949. Found: 469.8936. Calcd. for C$_{16}$H$_{11}$Cl$_3$O$_6$S: 435.9340, 435.9320.

EXAMPLE 36

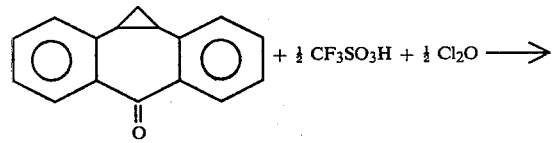

52

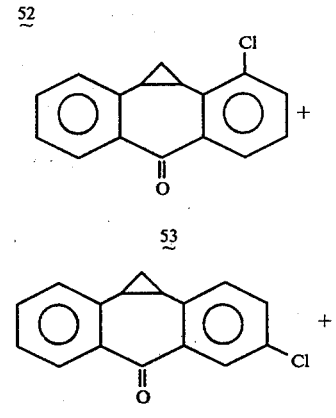

53

54

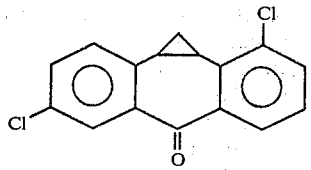

55

A solution of ketone 52 (0.88 g, 4.0 mmol) in CCl$_4$ (10 ml) was treated with trifluoromethanesulfonic acid (0.18 ml, 2.0 mmol) and the resulting yellow solution was treated with a solution of dichlorine monoxide in CCl$_4$ (2.0 mmol) while the temperature was kept below 20°. The mixture was stirred at room temperature for 45 min, added to water (100 ml) and extracted with CH$_2$Cl$_2$. The extract was washed with sodium bicarbonate, brine, and dried (MgSO$_4$). Evaporation gave 1.13 g of colorless oil. Recrystallization from ether/petroleum ether gave 200 mg of white solid whose $^1$H nmr spectrum (7.75–6.93 (m), 3.50–1.90 (m), and 0.83–0.45 (m)) was essentially identical with that of authentic ketone 53. The mother liquor was processed to give an additional 164 mg of solid which was ca. 70% ketone 53. HPLC purification of the mother liquors gave 108 mg of 52, 80 mg of ketone 53, 104 mg of chloro ketone 54, and 109 mg of a dichloro ketone believed to have structure 55 (mass spec: found 288.0104, calcd 288.0108). $^1$H nmr of ketone 54: 7.70–7.03 (m, area 224), 2.73–1.90 (m, area 94), 0.65–0.28 (m, area 30). $^1$H nmr of ketone 55: 7.67–7.00 (m, area 140), 3.50–3.00 (m, area 20), 2.87–1.93 (m, area 53), 0.77–0.38 (m, area 22). The cyclopropyl region was nearly identical with that of ketone 53.

EXAMPLE 37

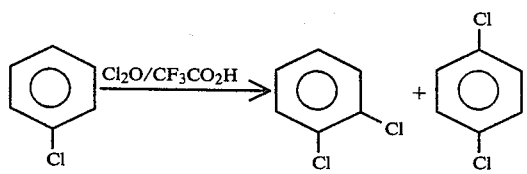

A solution of chlorobenzene (4.50 g, 40 mmol) and trifluoroacetic acid (20 ml) at 25° was treated dropwise with a solution of Cl$_2$O in CCl$_4$ (5 ml, 5 mmol). The mixture was stirred for 20 min, added to water, and extracted with CH$_2$Cl$_2$. The extract was washed with bicarbonate, brine, and dried, and concentrated. Glpc analysis (6'×¼"3% SE-30 at 110°) showed in addition to unreacted starting material a 60/40 mixture of p-dichlorobenzene/o-dichlorobenzene.

EXAMPLE 38

To a solution of anisole (1.62 g, 0.015 mole) and trichloroacetic acid (0.08 g, 5 wt %) in carbon tetrachloride (5 ml) was added chlorine monoxide (3.91 g, 0.045 mole) in carbon tetrachloride (43.1 ml) at 25°–30°. The brown color of chlorine monoxide disappeared after about four hours. The mixture after stirring at room temperature overnight was diluted with methylene chloride (20 ml) and washed with aqueous sodium bicarbonate. (Considerable insoluble material adhered to the walls of the reactor and was not recovered). The product was dried and the solvent removed on a rotary evaporator to give a mobile brown oil (2.83 g). Analysis of the product by Hnmr showed it contained considerable unidentified by-products. The product was separated by gas phase chromatography and the fractions were identified by mass spectrometric analysis as dichloroanisole (2 isomers 43.4%), trichloroanisole (25.8%), a small amount of tetrachloroanisole and several unidentified products.

This reaction was repeated using trifluoroacetic acid (25 ml) in place of trichloroacetic acid. The crude product (4.21 g) isolated in the same way was a crystalline solid containing a trace of oil. Hnmr analysis showed a singlet (δ3.8) suggesting that the product is substantially pure pentachloroanisole.

EXAMPLE 39

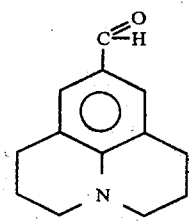

To 9-Julolidine (1.5 g, 0.0075 mole) in trifluoroacetic acid (20 ml) was added chlorine monoxide (0.34 g, 0.0038 mole) in carbon tetrachloride (4.5 ml) at 26°–32° C. After stirring overnight at room temperature the reaction mixture was diluted with methylene chloride (50 ml), washed with water and finally with aqueous sodium bicarbonate. The organic layer was dried and the solvent removed to give brown crystalline solid (1.95 g). Analysis by Hnmr showed a monochlorination of the aromatic ring in 60% yield.

EXAMPLE 40

To a solution of chlorobenzene (2.25 g, 0.02 mole) and trichloroacetic acid (0.113 g, 5 wt %) in carbon tetrachloride (5 ml) was added chlorine monoxide (0.87 g, 0.01 mole) in carbon tetrachloride (9.36 ml) at 25°–30° C. After stirring at room temperature 3 hrs, the product was washed with aqueous sodium bicarbonate, dried and the solvent removed to give a light yellow oil (0.69 g). Considerable insoluble material adhered to the walls of the reaction flask and was not recovered. Analysis of the yellow oil by Hnmr showed major and broad absorption at δ3.0 to 6.5 and less absorption as a singlet at δ7.20. The high field absorption results from by-product formation while the singlet at δ3.0 suggests some ring chlorination may have occurred. When the above experiment was repeated using a larger proportion of trichloroacetic acid (2.45 g, 0.015 mole), much less residue was formed; more product (2.2 g) was isolated. Analysis of the product by Hnmr gave a spectrum similar to that described above but much less by-product was indicated.

The initial experiment was repeated using chlorobenzene (2.25 g, 0.02 mole), trichloroacetic acid (0.113 g, 5 wt %) in carbon tetrachloride (5 ml) and chlorine monoxide (5.21 g, 0.06 mole) in carbon tetrachloride (56 ml). The product when isolated in the same manner (2.21 g) consisted of monochlorobenzene (14.8%), dichlorobenzene (77.7%) with small amounts of tri- and tetrachlorobenzene.

This experiment was again repeated using chlorobenzene (2.25 g, 0.02 mole), trifluoroacetic acid (25 ml) in carbon tetrachloride (5 ml) and chlorine monoxide (5.21 g, 0.06 mole) in carbon tetrachloride (57 ml). After stirring at room temperature overnight the mixture was filtered to separate white needles (0.69 g). The filtrate was washed with sodium bicarbonate, dried and the solvent removed on a rotary evaporator to give additional white crystalline solid (total wt 5.96 g); 100% yield. The product was identified as hexachlorobenzene by comparison of its infrared spectrum with that of an authentic sample.

Regarding the above examples, some of the products were separated by gas phase chromatography using either a Carbowax® 1500 on Carbopak® C column (60°/4 minutes and 8°/minute to 170°) or a SP 2250 column (60°-250° at 6°/minute). The products were identified by a Varian 3700 GC coupled to a VG Micromass 16 F. mass spectrometer.

BEST MODE FOR CARRYING OUT THE INVENTION

The best mode for carrying out the invention involves the use of a strong acid and a substituted aromatic compound whose substituents exhibit a strong net electronegative effect.

INDUSTRIAL APPLICABILITY

By means of the process of this invention can be prepared numerous nuclearly chlorinated aromatic compounds which are useful in the agrichemical and pharmaceutical fields.

It is to be understood that the above illustration and description of embodiments of the invention are not intended as limitations to the precise constructions herein disclosed and it is to be further understood that the right is reserved to all changes and modifications coming within the scope of the invention as defined herein.

I claim:

1. Process for nuclear chlorination of non-phenolic aromatic compounds, said process comprising contacting and reacting a non-phenolic aromatic compound having a net Hammett $\sigma$ value of about $-0.1$ to about 2.0 with chlorine monoxide in the presence of at least one half an equivalent amount, based on the chlorine monoxide, of an acid having a $pK_a$ no greater than that of trichloroacetic acid, provided, however, when the net Hammet $\sigma$ value is about 0.7 to about 2.0, the acid has a $pK_a$ no greater than that of trifluoroacetic acid.

2. Process of claim 1 wherein at least an equivalent amount of acid is present.

3. Process for nuclear chlorination of non-phenolic aromatic compounds, said process comprising contacting and reacting a non-phenolic aromatic compound having one or more substituents which provide a net effect that is electron-withdrawing with chlorine monoxide in the presence of at least one half an equivalent amount, based on the chlorine monoxide, of an acid having a $pK_a$ no greater than that of trifluoroacetic acid.

4. Process of claim 3 wherein at least an equivalent amount of acid is present.

5. Process for nuclear chlorination of non-phenolic aromatic compounds, said process comprising contacting and reacting a non-phenolic aromatic compound having a net Hammett $\sigma$ value of about $-0.1$ to about 2.0 with chlorine monoxide in the presence of at least one half an equivalent amount, based on the chlorine monoxide, of an acid having a $pK_a$ no greater than that of trichloroacetic acid, provided, however, when the net Hammett $\sigma$ value is about 0.7 to about 2.0, the acid has a $pK_a$ no greater than that of trifluoroacetic acid, said non-phenolic aromatic compound being of the formula selected from the group consisting of

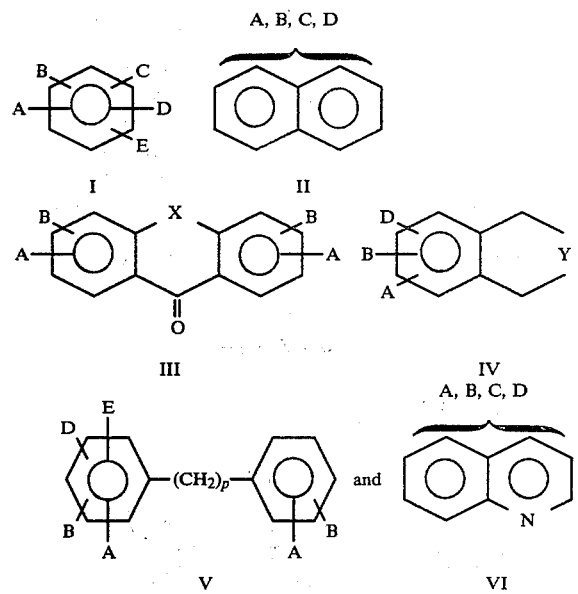

wherein:
each of A and B is independently selected from H, OR, $OCF_3$, $NH_2$, $NR_2$, $NR_3^\oplus$, $PR_3^\oplus$, $NO_2$, CN, F, Cl, Br, I, $CZ_3$,

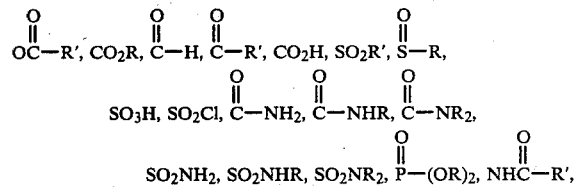

perfluoroalkyl of 1-8 carbon atoms, alkyl of 1-10 carbon atoms and alkyl of 1-10 carbon atoms substituted with any of the foregoing except H, perfluoroalkyl and alkyl;

C is H, OR, Cl, Br, F, $CZ_3$,

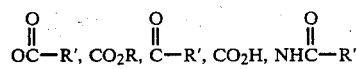

or alkyl of 1-10 carbon atoms;
D is H or Cl;
E is H or Cl;
R is alkyl of 1-10 carbon atoms or aryl;
R' is alkyl of 1-10 carbon atoms, aryl or $CZ_3$;
X is

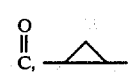

or $(CH_2)_n$;
Y is $(CH_2)_m$;

each Z is independently selected from Cl, Br, and F;
m is 3-6;
n is 0-3; and
p is 0-10,
provided, however, in III and V each of A and B is selected independently.

6. Process of claim 5 wherein at least an equivalent amount of acid is present.

7. Process for nuclear chlorination of non-phenolic aromatic compounds, said process comprising contacting and reacting a non-phenolic aromatic compound having one or more substituents which provide a net effect that is electron-withdrawing with chlorine monoxide in the presence of at least one half an equivalent amount, based on the chlorine monoxide, of an acid having a $pK_a$ no greater than that of trifluoroacetic acid, said non-phenolic aromatic compound being of the formula selected from the group consisting of

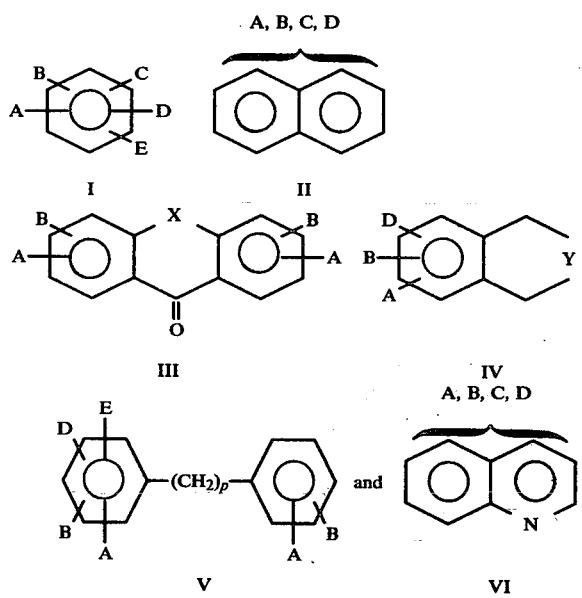

wherein:
each of A and B is independently selected from H, OR, OCF$_3$, NH$_2$, NR$_2$, NR$_3^\oplus$, PR$_3^\oplus$, NO$_2$, CN, F, Cl, Br, I, CZ$_3$,

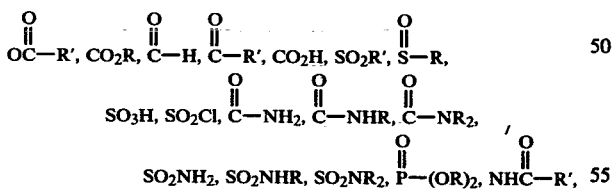

perfluoroalkyl of 1-8 carbon atoms, alkyl of 1-10 carbon atoms and alkyl of 1-10 carbon atoms substituted with any of the foregoing except H, perfluoroalkyl and alkyl;
C is H, OR, Cl, Br, F, CZ$_3$,

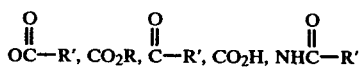

or alkyl of 1-10 carbon atoms;
D is H or Cl;
E is H or Cl;
R is alkyl of 1-10 carbon atoms or aryl;
R' is alkyl of 1-10 carbon atoms, aryl or CZ$_3$;
X is

or (CH$_2$)$_n$;
Y is (CH$_2$)$_m$; each Z is independently selected from Cl, Br, and F;
m is 3-6;
n is 0-3; and
p is 0-10,
provided, however, in III and V each of A and B is selected independently.

8. Process of claim 7 wherein at least an equivalent amount of acid is present.

9. Process of claim 5 wherein the non-phenolic aromatic compound is of formula I and C is H or Cl.

10. Process of claim 5 wherein: the non-phenolic compound is of formula I;
A is selected from H, OR", NH$_2$, NR"$_2$, NO$_2$, CN, Cl, CF$_3$, CCl$_3$, CO$_2$R",

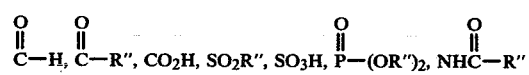

and alkyl of 1-4 carbon atoms;
B is selected from H, OR", NR"$_2$, NO$_2$, CN, Cl, CF$_3$, CCl$_3$, CO$_2$R",

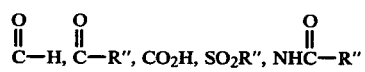

and alkyl of 1-4 carbon atoms; and
R" is alkyl of 1-4 carbon atoms.

11. Process of claim 10 wherein at least an equivalent amount of acid is present.

12. Process of claim 7 wherein the non-phenolic aromatic compound is of formula I and C is H or Cl.

13. Process of claim 7 wherein: the non-phenolic compound is of formula I;
A is selected from H, OR", NH$_2$, NR"$_2$, NO$_2$, CN, Cl, CF$_3$, CCl$_3$, CO$_2$R",

and alkyl of 1-4 carbon atoms;
B is selected from H, OR", NR"$_2$, NO$_2$, CN, Cl, CF$_3$, CCl$_3$, CO$_2$R",

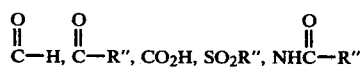

and alkyl of 1-4 carbon atoms; and
R" is alkyl of 1-4 carbon atoms.

14. Process of claim 13 wherein at least an equivalent amount of acid is present.

15. Process of claim 1 which is carried out at −40° to 100° C.

16. Process of claim 3 which is carried out at −40° to 100° C.

* * * * *